(12) United States Patent
Dennerlein

(10) Patent No.: US 11,151,772 B2
(45) Date of Patent: Oct. 19, 2021

(54) COMPUTER-IMPLEMENTED METHOD OF DERIVING 3D IMAGE DATA OF A RECONSTRUCTION VOLUME AND COMPUTER READABLE MEDIUM

(71) Applicant: Siemens Healthcare GmbH, Erlangen (DE)

(72) Inventor: Frank Dennerlein, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/985,357

(22) Filed: Aug. 5, 2020

(65) Prior Publication Data
US 2021/0049810 A1 Feb. 18, 2021

(30) Foreign Application Priority Data
Aug. 12, 2019 (EP) .................................... 19191233

(51) Int. Cl.
*G06T 11/00* (2006.01)
*A61B 6/03* (2006.01)
*G06T 15/08* (2011.01)

(52) U.S. Cl.
CPC ............ *G06T 15/08* (2013.01); *A61B 6/03* (2013.01); *G06T 11/006* (2013.01); *G06T 11/008* (2013.01); *G06T 2210/41* (2013.01); *G06T 2211/421* (2013.01)

(58) Field of Classification Search
None
See application file for complete search history.

(56) References Cited

U.S. PATENT DOCUMENTS

| 6,148,057 A * | 11/2000 | Urchuk | A61B 6/583 378/18 |
| 2011/0091085 A1* | 4/2011 | Dennerlein | G06T 11/006 382/131 |
| 2020/0311912 A1* | 10/2020 | Knoplioch | A61B 6/5258 |

OTHER PUBLICATIONS

Abdurahman S et al: "Optimizing High Resolution Reconstruction in Digital Breast Tomosynthesis Using Filtered Back Projection"; Breast Imaging. 12th International Workshop; IWDM 2014. Proceedings: LNCS 8539 Springer International Publishing Cham, Switzerland; 2014; pp: 520-527; XP055637234; ISBN: 978-3-319-07886-1; Jun. 2014.

(Continued)

*Primary Examiner* — Joni Hsu
(74) *Attorney, Agent, or Firm* — Harness, Dickey & Pierce, P.L.C.

(57) ABSTRACT

A computer-implemented method of deriving 3D image data of a reconstruction volume from a plurality of 2D projections by way of filtered back-projection is disclosed. An embodiment of the method includes receiving a plurality of 2D projections of an imaged object, each 2D projection corresponding to a projection plane; applying a filter to each of the 2D projections to yield filtered 2D projections; calculating a filtered back-projection density distribution from the filtered 2D projections; calculating at least one modified filtered back-projection density distribution indicative of outlier values included in the filtered 2D projections; and calculating a revised filtered back-projection density distribution as a weighted linear combination of the filtered back-projection density distribution and the at least one modified filtered back-projection density distribution.

21 Claims, 2 Drawing Sheets

(56) References Cited

OTHER PUBLICATIONS

Rodriguez-Ruiz Alejandro et al: "New reconstruction algorithm for digital breast tomosynthesis: better image quality for humans and computers"; Acta Radiologica (Stockholm, Sweden: 1987) Sep. 2018; vol. 59; No. 9; pp. 1051-1059, XP055638706; ISSN: 1600-0455.

Abdurahman, Shiras et al. "Out-of-Plane Artifact Reduction in Tomosynthesis Based on Regression Modeling and Outlier Detection" International Workshop on Digital Mammography, IWDM 2012, Breast Imaging, pp. 729-736, Lecture Notes in Computer Science, vol. 7361. Springer, Berlin, Heidelberg, 2012 // https://doi.org/10.1007/978-3-642-31271-7_94.

Rohkohl et al. "C-arm CT: Reconstruction of Dynamic High Contrast Objects Applied to the Coronary Sinus" IEEE Nuclear Science Symposium Conference Record 2008, pp. 5113-5120, NSS '08. IEEE (Oct. 19-25, 2008).

Extended European Search Report for Application No./Patent No. 19191233.6-1210, dated Nov. 15, 2019.

* cited by examiner

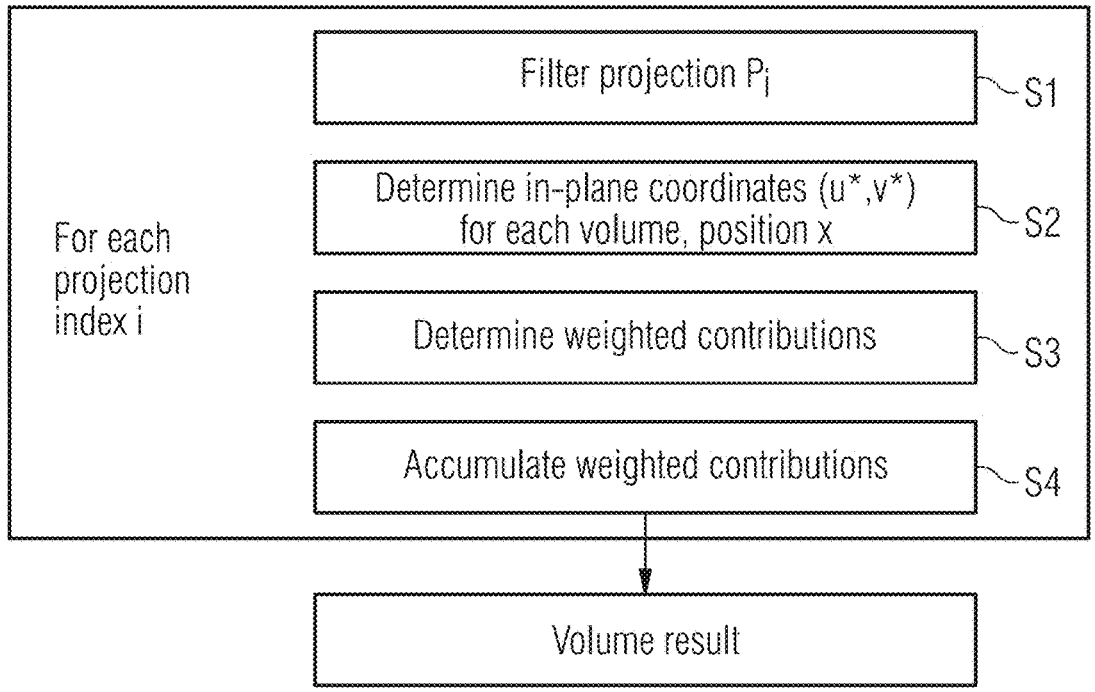
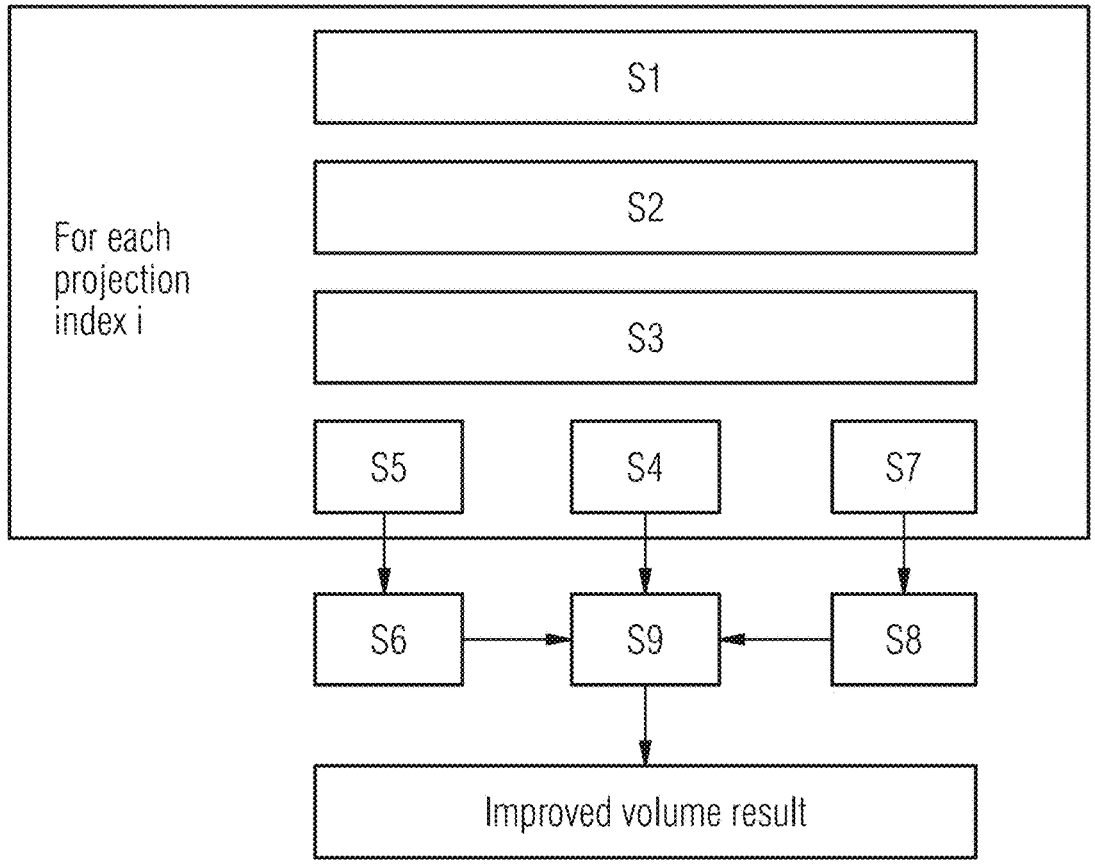

COMPUTER-IMPLEMENTED METHOD OF DERIVING 3D IMAGE DATA OF A RECONSTRUCTION VOLUME AND COMPUTER READABLE MEDIUM

PRIORITY STATEMENT

The present application hereby claims priority under 35 U.S.C. §119 to European patent application number EP 19191233.6 filed August 12, 2019, the entire contents of which are hereby incorporated herein by reference.

FIELD

Various example embodiments of the invention generally relate to a computer-implemented method of deriving 3D image data of a reconstruction volume from a plurality of 2D projections by way of filtered back-projection.

BACKGROUND

Deriving three-dimensional (3D) image data of a reconstruction volume from a set of captured two-dimensional (2D) projections by way of filtered back-projection is a well established method in the field of medical imaging. In particular, filtered back-projection is used in conventional computed tomography (CT) or in tomosynthesis applications to reconstruct 3D image data of a scanned object such as a part of the body of a patient, a piece of luggage or a manufactured component. The basis of such a reconstruction by way of filtered back-projection is a set of 2D projections (or: projection images) of the scanned object captured from different viewing angles. In CT applications, an x-ray emitter (or: x-ray tube, x-ray source) and an x-ray detector are typically rotated over the full angular range of 360° around the region of interest to capture a large number of 2D-projections from different viewing angles.

In tomosynthesis, the x-ray emitter usually does not perform a full 360 degrees rotation with respect to the scanned object. Typically, the restricted set of 2D projections underlying a tomosynthesis reconstruction corresponds to a scan over an angular sweep of about 30° to 90° around the scanned object. This limitation results in a mathematical insufficiency of the scanned data for an exact reconstruction. As a result, in particular tomosynthesis imaging suffers severely from artifacts that are induced by the restricted set of 2D projections underlying the calculations for 3D image reconstruction. These image artifacts are called cross-talk artifacts, streak artifacts, limited angle artifacts or out-of-plane artifacts and typically appear as disturbing, high-frequency, ripple-like structures in the reconstructed 3D image volume or in the image slices derived therefrom. Image artifacts may obscure important image details or corrupt regions that should actually be homogeneous. Cross-talk artifacts become especially visible when only a small number of projections are used.

Digital imaging may preferably be based on tomosynthesis techniques when the form factor of the investigated objects favors tomosynthesis scan set-ups over conventional CT set-ups. Additionally, the demand for high throughput may require fast scans with low projection numbers, like for example only about 16 2D projections per scan as compared to more than 500 2D projections typically obtained during a CT-scan.

The problem of reducing image artifacts in 3D image data derived from 2D projections by way of filtered back-projections has been addressed before. One approach includes using a different scan motion protocol with a larger tomosynthesis scan angle to reduce the degree of data insufficiency underlying the image reconstruction. Another approach includes using more 2D projections to blur high-frequency cross-talk artifact structures and thus make them less visible. Yet another approach includes applying specific artifact-reduction algorithms during reconstruction.

Increasing the tomosynthesis angle is often not a viable approach because the shape of the object under investigation may not allow for larger tomosynthesis angles due to possible collisions of the scanned object with a component of the imaging device or scanner. In certain applications, for example in homeland security applications, the scanners for capturing the projections of the scanned objects need to comply with limited space requirements. However, scanners with compact dimensions may not be suited to scan an object over a large angular region.

Increasing the number of 2D projections to blur high-frequency cross-talk artifact structures is often not a viable approach to reduce artifacts because of restrictions in scan time, in detector frame rate, in total projection data size or in computation time.

Applying specific artifact-reduction algorithms is in general favorable, since this approach involves computer-implemented methods which may readily be implemented by software. Various approaches have been proposed in the literature.

For example, iterative reconstruction methods together with some smoothing priors were introduced to reduce artifacts, in particular star-shaped cross-talk artifacts. However, iterative reconstruction is computationally very expensive and is sensitive to lateral data truncation.

Another approach relates to filtered back-projection methods with modified back-projection operators. These methods rely on the detection and rejection of outliers, in particularly of outliers having high and low values, during the step of accumulating different contributions of each of the input projections to a density value at a given volume (or: voxel) position. Outliers may cause the ripple-structure of cross-talk artifacts. Variants of this idea are described, for example, in "C-arm CT: Reconstruction of Dynamic High Contrast Objects Applied to the Coronary Sinus", Rohkohl et al., IEEE Nuclear Science Symposium and Medical Imaging Conference Record (Nuclear Science Symposium and Medical Imaging Conference Dresden, Germany 19-25 October 2008) 2008, pages 5113 to 5120 or in "Out-of-Plane Artifact Reduction in Tomosynthesis Based on Regression Modeling and Outlier Detection", Abdurahman et al, International Workshop on Digital Mammography IWDM 2012: Breast Imaging, pages 729 to 736.

SUMMARY

The inventors have discovered that while the approaches proposed in the cited references can be effective, they are computational and/or memory intensive in a real life implementation. Moreover, the inventors have discovered that the approach of Rohkohl et al. requires creating and keeping a sorted list of all contributions to the 3D image data at a given volume position during reconstruction to detect and eliminate outliers. In other cases, the rejection of outliers is based on a heuristic technique, which introduces simplifications to avoid memory-expensive sorted lists, but degrades the obtained results.

At least one embodiment of the present invention provides an efficient method for reducing cross-talk artifacts in 3D image data of a reconstruction volume derived by way of filtered back-projection.

At least one embodiment is directed to a computer-implemented method of deriving 3D image data of a reconstruction volume from a plurality of 2D projections by way of filtered back-projection.

At least one embodiment is directed to a computer-implemented method of deriving 3D image data of a reconstruction volume from a plurality of 2D projections by way of filtered back-projection comprises receiving a plurality of 2D projections of an imaged object, each 2D projection corresponding to a projection plane;

applying a filter to each of the 2D projections to yield filtered 2D projections; and calculating a filtered back-projection density distribution from the filtered 2D projections by way of filtered back-projection.

In at least one example embodiment of the computer-implemented method, calculating the at least one modified filtered back-projection density distribution that is indicative of outlier values included in the filtered 2D projections by way of filtered back-projection comprises:

defining at least one look-up table that overweighs outlier values in at least a relevant domain;

defining an inverted look-up table that is inverse to the look-up table;

determining, for each volume position in the reconstruction volume and for each 2D projection, two-dimensional in-plane coordinates by projecting the volume positions onto the projection plane defined by the 2D projections;

determining, for each volume position in the reconstruction volume and for each 2D projection, a modified weighted contribution of each of the filtered 2D projections, wherein determining the modified weighted contributions in particular includes evaluating the filtered 2D projections at the in-plane coordinates corresponding to the volume position and applying the look-up table to the filtered 2D projections evaluated at the in-plane coordinates; and accumulating, for each volume position in the reconstruction volume, the modified weighted contributions of the 2D projections corresponding to different projection planes and applying the inverted look-up table to the result to yield the modified filtered back-projection density distribution.

In at least one example embodiment of the computer-implemented method, calculating the at least one modified filtered back-projection density distribution indicative of high outlier values included in the filtered 2D projections comprises:

defining at least one first look-up table that overweighs high outlier values in at least a relevant domain;

defining an inverted first look-up table that is inverse to the first look-up table;

determining, for each volume position in the reconstruction volume and for each 2D projection, two-dimensional in-plane coordinates by projecting the volume positions onto the projection plane defined by the 2D projections;

determining, for each volume position in the reconstruction volume and for each 2D projection, a first modified weighted contribution of each of the filtered 2D projections, wherein determining the first modified weighted contributions includes evaluating the filtered 2D projections at the in-plane coordinates corresponding to the volume position and applying the first look-up table to the filtered 2D projections evaluated at the in-plane coordinates;

accumulating, for each volume position in the reconstruction volume, the first modified weighted contributions of the 2D projections corresponding to different projection planes and applying the inverted first look-up table to the result to yield the first modified filtered back-projection density distribution.

In at least one example embodiment of the computer-implemented method, calculating the at least one modified filtered back-projection density distribution indicative of low outlier values included in the filtered 2D projections comprises:

defining at least one second look-up table that overweighs high outlier values in at least a relevant domain;

defining an inverted second look-up table that is inverse to the second look-up table;

determining, for each volume position in the reconstruction volume and for each 2D projection, two-dimensional in-plane coordinates by projecting the volume positions onto the projection plane defined by the 2D projections;

determining, for each volume position in the reconstruction volume and for each 2D projection, a second modified weighted contribution of each of the filtered 2D projections, wherein determining the second modified weighted contributions includes evaluating the filtered 2D projections at the in-plane coordinates corresponding to the volume position and applying the second look-up table to the filtered 2D projections evaluated at the in-plane coordinates; and accumulating, for each volume position in the reconstruction volume, the second modified weighted contributions of the 2D projections corresponding to different projection planes and applying the inverted second look-up table to the result to yield the second modified filtered back-projection density distribution.

In at least one example embodiment of the computer-implemented method, calculating the filtered back-projection density distribution from the filtered 2D projections by way of filtered back-projection comprises:

determining, for each volume position in the reconstruction volume and for each 2D projection, two-dimensional in-plane coordinates by projecting the volume positions onto the projection plane defined by each of the 2D projections;

determining, for each volume position in the reconstruction volume and for each 2D projection, a weighted contribution of each of the filtered 2D projections, wherein determining the weighted contributions includes evaluating the filtered 2D projections at the in-plane coordinates corresponding to the volume position;

calculating a filtered back-projection density distribution from the filtered 2D projections by accumulating the weighted contributions of the 2D projections corresponding to different projection planes.

At least one example embodiment of the invention further relates to a computer readable medium comprising instructions, which, when executed on a processor, computer or computing unit, causes the processor, computer or computing unit to carry out the computer-implemented method of at least one embodiment as described herein before.

A computer readable medium may in particular comprise a physical storage medium. In other embodiments, the computer readable medium may be embodied as sequence of signals that may in particular be made available via download over a network, like, for example, the internet.

At least one example embodiment of the invention further relates to a computer program product comprising instructions, which, when executed on a processor, computer or computing unit, causes the processor, computer or computing unit to carry out the computer-implemented method of at least one embodiment as described herein before.

At least one example embodiment of the invention further relates to an imaging system comprising at least one imaging modality configured to capture a plurality of 2D projections of an imaged object, and at least one of a computer, processor and computing unit configured to receive the 2D projections as input data. The computer, processor and computing unit executes the instructions of the aforementioned computer readable medium or computer program product or is otherwise configured to derive 3D image data of the reconstruction volume from the plurality of 2D projections by way of any of the computer-implemented methods of at least one embodiment as described herein before.

BRIEF DESCRIPTION OF THE DRAWINGS

The invention is described in more detail with reference to example embodiments that are illustrated in the figures, in which:

FIG. 1 shows a flowchart of a computer-implemented method of deriving 3D image data from a plurality of 2D projections by way of filtered back-projection;

FIG. 2 shows a flowchart of a revised computer-implemented method of deriving 3D image data from a plurality of 2D projections by way of filtered back-projection;

Identical or corresponding parts or components are indicated in all figures by the same reference numerals.

DETAILED DESCRIPTION OF THE EXAMPLE EMBODIMENTS

Figure 3:
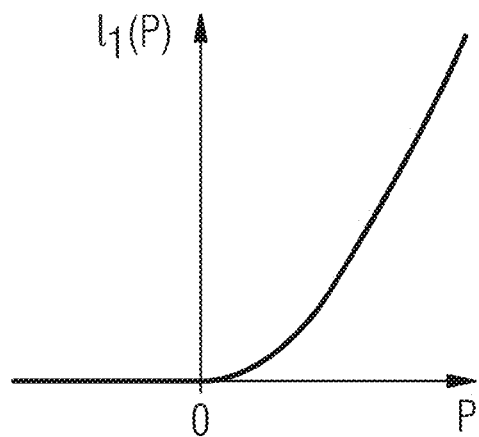
FIG. 3 illustrates qualitatively a possible choice of a first look-up table for the revised method of FIG. 2.

The above and other elements, features, steps, and concepts of the present disclosure will be more apparent from the following detailed description in accordance with example embodiments of the invention, which will be explained with reference to the accompanying drawings.

Some examples of the present disclosure generally provide for a plurality of circuits, data storages, connections, or electrical devices such as e.g. processors. All references to these entities, or other electrical devices, or the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection, or communication, or coupling between functional blocks, devices, components, or other physical or functional units shown in the drawings or described herein may also be implemented by an indirect connection or coupling. A communication between devices may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, O Caml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a computer-implemented method of deriving 3D image data of a reconstruction volume from a plurality of 2D projections by way of filtered back-projection comprises receiving a plurality of 2D projections of an imaged object, each 2D projection corresponding to a projection plane;

applying a filter to each of the 2D projections to yield filtered 2D projections; and calculating a filtered back-projection density distribution from the filtered 2D projections by way of filtered back-projection.

At least one embodiment is directed to a the invention, the computer-implemented method further comprises calculating at least one modified filtered back-projection density distribution that is indicative of outlier values included in the filtered 2D projections by way of filtered back-projection;

calculating a revised filtered back-projection density distribution as a weighted linear combination of the filtered back-projection density distribution and the at least one modified filtered back-projection density distribution.

The suggested computer-implemented method efficiently reduces star-shaped cross-talk artifacts in particular in tomosynthesis imaging that relies on a restricted set of 2D projections and/or relating to low projection counts. The computer-implemented method can easily be implemented in available imaging apparatuses or imaging systems by way of software. In particular, the computer-implemented method is adapted to be used in medical or non-medical imaging, for example in the field of 3D image guided surgery, mammography, cardiology or orthopedics. Even more particularly, pediatric use-cases are foreseen, because the suggested method is configured to improve the image quality of 3D reconstructions derived from a low number of 2D projections.

Since the suggested computer-implemented method is particularly suited for dealing with low projection counts, it may help to improve the attractiveness of tomosynthesis imaging over full CT or cone-beam CT imaging approaches. Applications of the computer-implemented method in both medical and non-medical fields, in particular in the field of industrial CT, electronic or scientific imaging, veterinary, dental or even homeland security applications, are foreseen.

The 2D projections underlying the reconstruction of the density distribution of the imaged object may be captured by any suitable imaging modality. In general, each 2D projection corresponds to a projection plane that may in particular be defined by the imaging geometry of the imaging modality. Even more particularly, the projection plane of each of the 2D projections may be defined by the size, location and orientation of the detector capturing the respective 2D projection, in particular with respect to a radiation source, like, for example, an x-ray source.

Applying a filter to each of the 2D projections to yield filtered 2D projections is in general an established technique in the field of filtered back-projection. The filtered back-projection density distribution calculated from the filtered 2D projections may be viewed as an approximation to the three dimensional density distribution of the scanned object. In this sense, the filtered back-projection density distribution may be considered as volume data or simply as a volume that attributes volume positions (or: volume coordinates, voxel coordinates) to density values. The filtered back-projection density distribution in particular may contain image artifacts that originate from (high or low) outlier values.

One core idea of at least one embodiment of the suggested computer-implemented method relates to the creation of at least another volume that is indicative of outlier values that may cause image artifacts. This volume, which is referred to as the at least one modified filtered back-projection density distribution, is also derived from the 2D projections by way filtered back-projection, but in a manner that it includes mostly contributions originating from outlier values. The at least one modified filtered back-projection density distribution thus in general shows stronger cross-talk artifacts than the regular reconstruction, which may be represented by the filtered back-projection density distribution. Instead of identifying and omitting the contribution of outliers during the reconstruction of the volumes, the present invention suggests constructing at least one additional volume that is indicative of the outlier values. By calculating the weighted linear combination of the filtered back-projection density distribution and the at least one modified filtered back-projection density distribution, the influence of outlier contributions may be reduced. As a result, the revised filtered back-projection density distribution may contain less artifacts that stem from outliers than the (regular) filtered back-projection density distribution.

The computer-implemented method for reducing artifacts in 3D image data, in particular in tomosynthesis applications, does not require any modifications of the imaging or scanning process. The suggested computer-implemented method may thus be immediately applied to established imaging and scanning techniques or apparatuses. Moreover, the computer-implemented method facilitates application of fast tomosynthesis data acquisitions workflows involving a relative low number of 2D projections. The suggested approach is computationally efficient, as the calculations only require point-wise operations on pixels or voxels. The calculations and results of the standard reconstruction by way of filtered back-projection may be accessed and included to compute a revised volume with less artifacts. The artifact reduction of the suggested computer-implemented method is comparable to the level of artifact reduction of other approaches, which are computationally more demanding. The suggested computer-implemented method does not require significantly more powerful hardware in terms of computational power or memory as compared to the established standard approaches utilizing filtered back-projection for deriving 3D image data from a set of 2D projections.

The computer-implemented method according to at least one embodiment of the invention may be applied in various different fields and may in particular be used in medical and non-medical applications. The computer-implemented method according to at least one embodiment of the invention is in particular suited for being used in combination with an image reconstruction based on tomography or, preferably, tomosynthesis. Medical applications in particular include, amongst others, a mammography, a computed tomography, an angiography, a fluoroscopy or a dental application. Non-medical applications may relate to industrial computed tomography scanning, laminography or homeland security applications.

Homeland security applications in particular may involve scanning of objects such as cargo, freight or luggage. Other non-medical applications relate to the investigation of goods, in particular of fabricated parts or components, by way of non-destructive measurements. The fabricated parts or manufactured components may in particular be manufactured by way of conventional or generative manufacturing processes. Conventional manufacturing processes may in particular involve milling, molding, welding, soldering or forming techniques. Generative (or: additive) manufacturing processes may in particular involve selective laser melting, selective laser sintering, 3D printing or similar techniques, in particular rapid prototyping techniques. Image reconstruction based on tomographic or tomosynthesis methods using the computer-implemented method of the invention may in particular be applied in the field of manufacturing control or inspection, for example to assess the quality of a manufactured component. The inspected component may in particular be an electronic component, such as a circuit board, printed circuit board (PCB), microchip, microcontroller or processor.

In at least one example embodiment of the computer-implemented method, calculating the at least one modified filtered back-projection density distribution that is indicative of outlier values included in the filtered 2D projections by way of filtered back-projection comprises:

defining at least one look-up table that overweighs outlier values in at least a relevant domain;

defining an inverted look-up table that is inverse to the look-up table;

determining, for each volume position in the reconstruction volume and for each 2D projection, two-dimensional in-plane coordinates by projecting the volume positions onto the projection plane defined by the 2D projections;

determining, for each volume position in the reconstruction volume and for each 2D projection, a modified weighted contribution of each of the filtered 2D projections, wherein determining the modified weighted contributions in particular includes evaluating the filtered 2D projections at the in-plane coordinates corresponding to the volume position and applying the look-up table to the filtered 2D projections evaluated at the in-plane coordinates; and accumulating, for each volume position in the reconstruction volume, the modified weighted contributions of the 2D projections corresponding to different projection planes and applying the inverted look-up table to the result to yield the modified filtered back-projection density distribution.

The at least one look-up table may be in particular be chosen to increase the contribution of outliers in the (filtered) 2D projections. These contributions are given additional weight during the accumulation step. The inverse to the at least one look-up table is applied to the accumulated result that includes contributions of all of the different 2D projections to yield the modified filtered back-projection density distribution. The modified filtered back-projection density distribution thus includes strong artifacts that originate from outlier contributions. Hence, the modified filtered back-projection density distribution is indicative of outlier values included in the filtered 2D projections.

Contributions to the density value at a given volume position of the reconstruction volume are determined by way of back projection. In particular, the (two dimensional) in-plane coordinates in the projection plane of each of the 2D projections that correspond to a given (three dimensional) volume position of a voxel in the reconstruction volume may be determined by projecting the volume position onto the respective projection planes.

Numerous choices for and variations of the at least one look-up table are possible and foreseen.

In at least one example embodiment of the computer-implemented method, the at least one look-up table is at least in parts determined by the characteristics of a function.

In at least one example embodiment of the computer-implemented method, the characteristics of the function determining the at least one look-up table at least in parts is at least one of a slope of the function, a curvature of the function and a zero of the function.

In at least one example embodiment of the computer-implemented nmethod, the function determining the at least one look-up table is at least in parts a polynomial function, a monomial function or a power function. In other embodiments, the at least one look-up table may be derived from other suitable, in particular monotonic, functions.

In at least one example embodiment of the computer-implemented method, the at least one look-up table is globally defined or depends on the 2D projection or on a sub-region within the 2D projection. In other words, the at least one look-up table may in particular be chosen such that the result of the application of the at least one look-up table to the filtered 2D projection is independent of a projection index labeling the different projections and the in-plane coordinates characterizing positions within the respective 2D projection. In other embodiments, the at least one look-up table may in particular be chosen such that the result of the application of the at least one look-up table to the filtered 2D projection is dependent on a projection index labeling the different projections and/or the in-plane coordinates characterizing positions within the respective 2D projection.

In at least one example embodiment of the computer-implemented method, the revised filtered back-projection density distribution is calculated as a weighted linear combination of the filtered back-projection density distribution and at least two modified filtered back-projection density distributions. At least one of the modified filtered back-projection density distributions is indicative of high outlier values included in the filtered 2D projections. At least another one of the modified filtered back-projection density distributions is indicative of low outlier values included in the filtered 2D projections. In other words, two separate volumes (modified filtered back-projection density distributions) are constructed that respectively are indicative of high and low outlier values.

In at least one example embodiment of the computer-implemented method, calculating the at least one modified filtered back-projection density distribution indicative of high outlier values included in the filtered 2D projections comprises:

defining at least one first look-up table that overweighs high outlier values in at least a relevant domain;

defining an inverted first look-up table that is inverse to the first look-up table;

determining, for each volume position in the reconstruction volume and for each 2D projection, two-dimensional in-plane coordinates by projecting the volume positions onto the projection plane defined by the 2D projections;

determining, for each volume position in the reconstruction volume and for each 2D projection, a first modified weighted contribution of each of the filtered 2D projections, wherein determining the first modified weighted contributions includes evaluating the filtered 2D projections at the in-plane coordinates corresponding to the volume position and applying the first look-up table to the filtered 2D projections evaluated at the in-plane coordinates; and accumulating, for each volume position in the reconstruction volume, the first modified weighted contributions of the 2D projections corresponding to different projection planes and applying the inverted first look-up table to the result to yield the first modified filtered back-projection density distribution.

The at least one first look-up table may in particular be chosen to increase the contribution of high (positive) outliers in the (filtered) 2D projections. These contributions are given additional weight during the accumulation step. The inverse to the at least one first look-up table is applied to the accumulated result that includes contributions of all of the different 2D projections to yield the first modified filtered back-projection density distribution. The different 2D projections may in particular be labeled by a projection index. The first modified filtered back-projection density distribution includes strong artifacts that originate from high positive outlier contributions. Hence, the first modified filtered back-projection density distribution is indicative of high (positive) outlier values included in the filtered 2D projections.

In at least one example embodiment of the computer-implemented method, calculating the at least one modified filtered back-projection density distribution indicative of low outlier values included in the filtered 2D projections comprises:
defining at least one second look-up table that overweighs high outlier values in at least a relevant domain;
defining an inverted second look-up table that is inverse to the second look-up table;
determining, for each volume position in the reconstruction volume and for each 2D projection, two-dimensional in-plane coordinates by projecting the volume positions onto the projection plane defined by the 2D projections;
determining, for each volume position in the reconstruction volume and for each 2D projection, a second modified weighted contribution of each of the filtered 2D projections, wherein determining the second modified weighted contributions includes evaluating the filtered 2D projections at the in-plane coordinates corresponding to the volume position and applying the second look-up table to the filtered 2D projections evaluated at the in-plane coordinates; and
accumulating, for each volume position in the reconstruction volume, the second modified weighted contributions of the 2D projections corresponding to different projection planes and applying the inverted second look-up table to the result to yield the second modified filtered back-projection density distribution.

The at least one second look-up table may in particular be chosen to increase the contribution of low (negative) outliers in the (filtered) 2D projections. These contributions are given additional weight during the accumulation step. The inverse to the at least one second look-up table is applied to the accumulated result that includes contributions of all of the different 2D projections to yield the modified filtered back-projection density distribution. The different 2D projections may in particular be labeled by a projection index. The second modified filtered back-projection density distribution includes strong artifacts that originate from low (negative) outlier contributions. Hence, the second modified filtered back-projection density distribution is indicative of high positive outlier values included in the filtered 2D projections.

In at least one example embodiment of the computer-implemented method, the 3D image data is a tomography or tomosynthesis reconstruction from the plurality of 2D projections. In case of a tomography reconstruction, the set of 2D projections typically includes several hundred, for example about 500 projections. In case of a tomosynthesis reconstruction, the set of 2D projections may be restricted and only include a few 2D projections, for example about 16 2D projections, taken from different angles.

In at least one example embodiment of the computer-implemented method, the plurality of 2D projections is a tomography or tomosynthesis image data set, in particular an image data set obtained via medical or non-medical imaging, for example via a mammography, a computed tomography, a positron emission tomography, a single-photon emission computed tomography, an industrial computed tomography, a non-destructive testing of a fabricated or manufactured good or a homeland security application.

In at least one example embodiment of the computer-implemented method, calculating the filtered back-projection density distribution from the filtered 2D projections by way of filtered back-projection comprises:
determining, for each volume position in the reconstruction volume and for each 2D projection, two-dimensional in-plane coordinates by projecting the volume positions onto the projection plane defined by each of the 2D projections;
determining, for each volume position in the reconstruction volume and for each 2D projection, a weighted contribution of each of the filtered 2D projections, wherein determining the weighted contributions includes evaluating the filtered 2D projections at the in-plane coordinates corresponding to the volume position;
calculating a filtered back-projection density distribution from the filtered 2D projections by accumulating the weighted contributions of the 2D projections corresponding to different projection planes.

Contributions to the density value represented by the filtered back-projection density distribution at a given volume position of the reconstruction volume are determined by way of back projection. In particular, the (two-dimensional) in-plane coordinates in the projection plane of each of the 2D projections that correspond to a given (three-dimensional) volume position of a voxel in the reconstruction volume may be determined by projecting the volume position onto the respective projection plane. The respective 2D projections and projection planes may in particular be labeled by a projection index. Contributions to the density value at a given volume position from different 2D projections may be accumulated to yield the filtered back-projection density distribution.

In at least one example embodiment of the computer-implemented method, calculating the revised filtered back-projection density distribution as the weighted linear combination of the filtered back-projection density distribution and the at least one modified filtered back-projection density distribution includes determining at least one weight for the at least one modified filtered back-projection density distribution. The at least one weight is globally defined or depends on a sub-region of the reconstruction volume.

In at least one example embodiment of the computer-implemented method, the at least one weight is determined by way of a volume-domain cost function. The volume-domain cost function may in particular be constructed with respect to attributes relating to the quality of the reconstructed in image, like the homogeneity or contrast, in certain regions. Application of the volume-domain cost function may in particular involve applying a gradient to the filtered back-projection density distribution or a variation of the weights, in particular to yield results that are optimized with respect to an image attribute indicative of the quality of the reconstructed image. The volume-domain cost function may relate to denoising, in particular to total variation denoising or total variation regularization.

At least one example embodiment of the invention further relates to a computer readable medium comprising instructions, which, when executed on a processor, computer or computing unit, causes the processor, computer or computing unit to carry out the computer-implemented method of at least one embodiment as described herein before.

A computer readable medium may in particular comprise a physical storage medium. In other embodiments, the computer readable medium may be embodied as sequence of signals that may in particular be made available via download over a network, like, for example, the internet.

At least one example embodiment of the invention further relates to a computer program product comprising instructions, which, when executed on a processor, computer or computing unit, causes the processor, computer or computing unit to carry out the computer-implemented method of at least one embodiment as described herein before.

At least one example embodiment of the invention further relates to an imaging system comprising at least one imaging modality configured to capture a plurality of 2D projections of an imaged object, and at least one of a computer, processor and computing unit configured to receive the 2D projections as input data. The computer, processor and computing unit executes the instructions of the afore-mentioned computer readable medium or computer program product or is otherwise configured to derive 3D image data of the reconstruction volume from the plurality of 2D projections by way of any of the computer-implemented methods of at least one embodiment as described herein before.

FIG. 1 depicts a flowchart of a computer-implemented method of deriving 3D image data from a plurality of 2D projections by way of filtered back-projection.

The computer-implemented method may in particular be applied to a tomosynthesis reconstruction of 3D image data from a restricted set of 2D projections. The restricted set of 2D projections may in particular correspond to a scan about the scanned object over a restricted angular range, for example over an angular range of 30° to 90° and/or a low number of 2D projections in the set. The computer-implemented method is in particular configured to yield 3D data with reduced artifacts when the reconstruction is based on such a restricted set of 2D projections.

The computer-implemented method is based on a number of 2D projections $P_i$ of an imaged object such as a scanned part of the body of a patient.

The term $P_i(u,v)$ denotes the 2D projection $P_i$ with projection index i. The projection index i is natural number ($i \in 1, \ldots, N$) and labels the different 2D projections $P_i$. The projection index i may in particular label 2D projections $P_i$ from different angles. For tomographic reconstructions, N may be large (for example N=100 to 1000). For tomosynthesis re-constructions, N may be relatively small (for example N=10 to 50). The entities (u, v) are two-dimensional coordinates de-fined by the detector capturing the i-th 2D projection $P_i$.

The term f(x) denotes a filtered back-projection density distribution f that approximates density values of the true density distribution of the imaged object at the volume (spatial, voxel) coordinates x.

Typically, the filtered back-projection density distribution f is calculated as follows:

In a first step S1, a filter is applied to each of the 2D projections $P_i(u,v)$ to yield corresponding filtered 2D projections $\hat{P}_i(u,v)$. The filtered 2D projections $\hat{P}_i(u,v)$ may in particular be ramp-filtered projections.

In a second step S2, in-plane coordinates (u*,v*) that correspond to volume positions x are determined. This is done for all volume positions x and for every 2D projection labeled by the projection index i. The in-plane coordinates (u*,v*) are in particular determined by projecting the voxels located at volume positions x onto the projection plane defined by a detector capturing the i-th 2D projection Pi. The projection geometry may in particular be defined by the imaging geometry of the imaging modality used for capturing the 2D projections Pi. In some embodiments, projecting the voxel on the projecting plane relating to the 2D projection Pi may include a perspective, orthogonal fan-parallel or semi-perspective projection.

In a third step S3, a weighted contribution of each filtered 2D projection to the density values is computed. The weighted contribution may in particular be computed as $$\frac{1}{ND(i,x)} \hat{P}_i(u^*, v^*)$$

where the back-projection weight D depends on the projection index i and a geometric factor that is dependent on the volume position x. In some particular embodiments, the back-projection weight D depends on the geometry of the imaging modality capturing the projections Pi. In particular, the back-projection weight D may depend on the geometric distance between an x-ray source used for capturing the i-th 2D projection $P_i$ and the volume position x. The entity N relates the total number of filtered 2D projections $\hat{P}_i$ in the set.

Steps S1 to S3 are repeated for each 2D projection $P_i$ labeled by projection index i.

The filtered back-projection density distribution f is calculated by accumulating the weighted contributions of the 2D projections that contribute to the density value at volume location x. In particular, the filtered back-projection density distribution f is calculated as a sum over all weighted contributions labeled by the projection index i:

$$f(x) = \sum_{i=1}^{N} \frac{1}{ND(i,x)} \hat{P}_i(u^*, v^*)$$

The filtered back-projection density distribution f is derived by way of filtered back-projection and provides a first approximation to the density values at the volume (voxel) positions x of the true density distribution of the imaged object. This approximation to the density distribution may in particular contain visual artifacts that for example originate from the fact that the restricted data (2D projections) underlying the calculation is insufficient for an exact reconstruction.

A refinement to the first approximation given by filtered back-projection density distribution f can be computed as $$f_{impr}(x) = f(x) - w_1 f_{c1}(x) - w_2 f_{c2}(x).$$

The term $f_{impr}$ denotes a revised filtered back-projection density distribution that is calculated as a weighted linear combination of the filtered back-projection density distribution f and the modified filtered back-projection density distributions $f_{c1}$, $f_{c2}$. The factors $w_1$, $w_2$ are weights.

FIG. 2 shows a flowchart for the computer-implemented method for deriving 3D image data of the reconstruction volume that includes the calculation of the revised filtered back-projection density distribution $f_{impr}$ as a weighted linear combination of the filtered back-projection density distribution f and the at least one modified filtered back-projection density distribution $f_{c1}$, $f_{c2}$ as described herein before. The steps S1 to S4 are identical to the steps S1 to S4 described herein before with reference to FIG. 1.

The modified filtered back-projection density distributions $f_{c1}$, $f_{c2}$ may in particular be computed as follows:

$$f_{C1}(x) = \hat{l}_1 \left( \sum_{i=1}^{N} \frac{1}{ND(i,x)} \frac{l_1(\hat{P}_i(u^*, v^*))}{\hat{P}_i(u^*, v^*)} \hat{P}_i(u^*, v^*) \right)$$

$$f_{C2}(x) = \hat{l}_2 \left( \sum_{i=1}^{N} \frac{1}{ND(i,x)} \frac{l_2(\hat{P}_i(u^*, v^*))}{\hat{P}_i(u^*, v^*)} \hat{P}_i(u^*, v^*) \right)$$

The term $l_1$ denotes a first look-up table. The term $\hat{l}_1$ denotes the inverse of the first look-up table $l_1$. Like-wise, $l_2$ denotes a second look-up table and $\hat{l}_2$ the inverse of the second look-up table $l_2$. If $A\hat{P}_i(u^*, v^*)$ equals 0, the weights in the formulas above are set to 0.

The first and second look-up tables $l_1$, $l_2$ are chosen such that outlier values included in the 2D projections $P_i$ are given additional weight. The idea behind the look-up-tables $l_1$, $l_2$ is that they define modified weights during the accumulation of contributions when the modified filtered back-projection density distributions $f_{c1}$, $f_{c2}$ are computed. These weights are selected to emphasize the impact of outlier contributions, as it is foreseen that those outliers may cause cross-talk artifacts. The modified filtered back-projection density distributions $f_{c1}$, $f_{c2}$ thus contain stronger cross-talk artifacts than the normal reconstruction. By computing the revised filtered back-projection density distribution $f_{impr}$ as the weighted linear combination of the filtered back-projection density distribution f and the modified filtered back-projection density distributions $f_{c1}$, $f_{c2}$, the impact of cross-talk artifacts can be reduced. In particular, the idea is to subtract the modified correction volumes $f_{c1}$, $f_{c2}$ from the standard reconstruction volume f obtained by filtered back-projection as outlined herein before in order to reduce the artifact level in the revised reconstruction volume $f_{impr}$.

The first look-up table $l_1$ may in particular be selected to overweigh high outlier values present in the 2D projections $P_i$. For example, the first look-up table $l_1$ may be determined by the expression $l_1(P) = P^5$ for $P > 0$ and 0 otherwise to select high outlier values. The inverse first look-up table $\hat{l}_1$ is the given by the expression $\hat{l}_1(f) = f^{1/5}$ for $f > 0$ and 0 otherwise.

In this particular embodiment, the first look-up table $l_1$ is chosen to overweigh large positive outlier values. Variations to this particular choice of the first look-up table $l_1$ are possible and within the scope of the present invention. In particular, the first look-up table $l_1$ may exhibit a different functional behavior. The function determining the first look-up table $l_1$ may in particular exhibit different characteristics, like, for example a different slope, curvature, and/or zero.

The second look-up table $l_2$ may in particular be selected to overweigh low outlier values present in the 2D projections $P_i$. For example, the first look-up table $l_2$ may be determined by the expression $l_2(P) = -|P|^5$ for $P < 0$ and 0 otherwise to select low outlier values. The inverse second look-up table $\hat{l}_2$ is the given by the expression $\hat{l}_2(f) = -|f|^{1/5}$ for $f < 0$ and 0 otherwise.

In this particular embodiment, the second look-up table $l_2$ is chosen to overweigh large negative outlier values. Variations to this particular choice of the second look-up table $l_2$ are possible and within the scope of the present invention. In particular, the second look-up table $l_2$ may exhibit a different functional behavior. The function determining the second look-up table $l_2$ may in particular exhibit different characteristics, like, for example a different slope, curvature, and/or zero.

Figure 4:
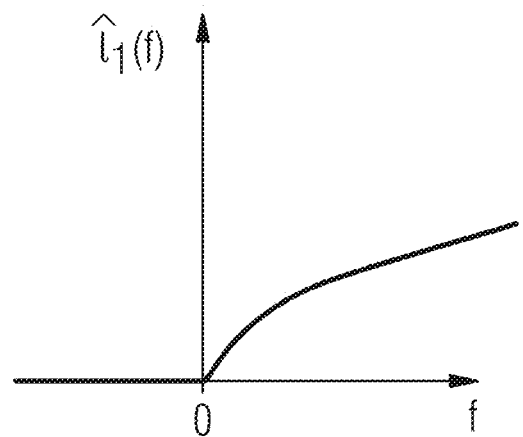
FIG. 4 illustrates qualitatively the inverse of the first look-up table of FIG. 3.
Figure 5:
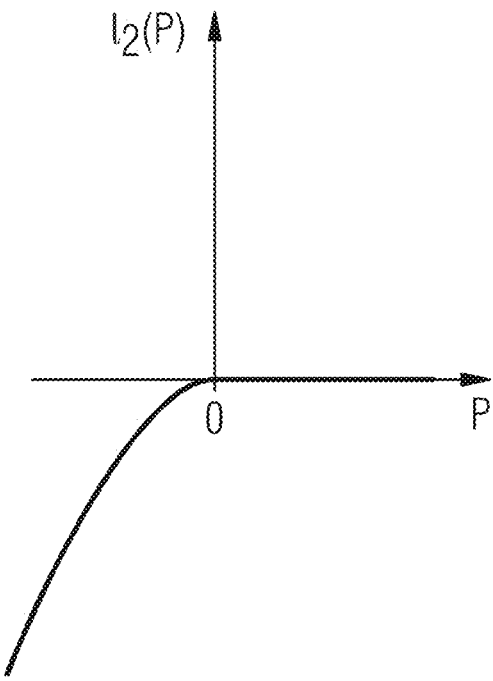
FIG. 5 illustrates qualitatively a possible choice of a second look-up table for the revised method of FIG. 2.
Figure 6:
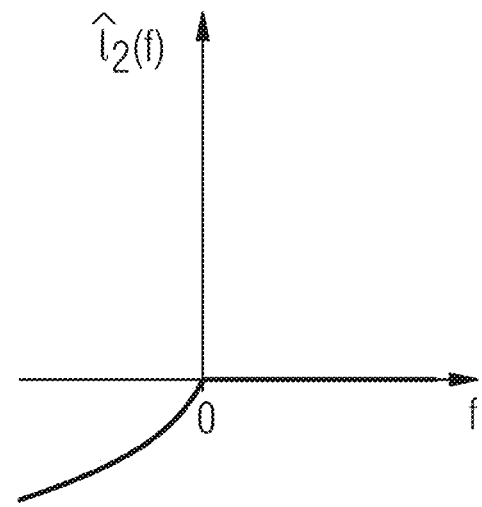
FIG. 6 illustrates qualitatively the inverse of the second look-up table of FIG. 5.

Possible choices for the first and second look-up tables $l_1$, $l_2$ are also illustrated in FIGS. 3 to 6.

The computation of the revised filtered back-projection density $f_{impr}$ as a weighted linear combination of the filtered back-projection density distribution f and the modified filtered back-projection density distributions $f_{c1}$, $f_{c2}$ is computationally efficient, as it in particular only requires pointwise operations on pixels and voxels indicated by in-plane coordinates $(u^*, v^*)$ and volume positions x. In comparison to the computer-implemented method described herein before with respect to FIG. 1, the total memory requirement of the revised method (see FIG. 2) is about three times, since the three volumes f(x), $f_{c1}(x)$, $f_{c2}(x)$ need to be kept during the reconstruction process. This is far less compared to keeping a sorted list of all N contributions labeled by the projection index i for each volume position x, which may be required in methods that rely on detecting and rejecting outlier values during the accumulation step.

The computation of the revised filtered back-projection density $f_{impr}$ may be implemented as follows: In step S5, the first look-up table $l_1$ is applied to the filtered projection $\hat{P}_i$ at in-plane coordinates $(u^*, v^*)$. This is done for every projection $\hat{P}_i$ labeled by projection index i and for every volume position x determining the respective in-plane coordinates $(u^*, v^*)$. The in-plane coordinates $(u^*, v^*)$ are determined as herein described before with respect to step S2.

Applying the first look-up table $l_1$ to the filtered projection $\hat{P}_i$ at in-plane coordinates $(u^*, v^*)$ and weighting the result with the back-projection weight D and N yields modified weights of the form $$\frac{1}{ND(i,x)} \frac{l_1(\hat{P}_i(u^*, v^*))}{\hat{P}_i(u^*, v^*)}.$$

These modified weights weight the filtered projection $\hat{P}_i$ as modified weighted contributions of the form $$\sum_{i=1}^{N} \frac{1}{ND(i,x)} \frac{l_1(\hat{P}_i(u^*, v^*))}{\hat{P}_i(u^*, v^*)} \hat{P}_i(u^*, v^*).$$

In step S5, these modified weighted contributions are accumulated by carrying out the sum over the projection index i.

In step 6, the inverse first look-up table $\hat{l}_1$ is applied to this result to yield the modified filtered back-projection density distributions $f_{c1}$ as $$f_{C1}(x) = \hat{l}_1 \left( \sum_{i=1}^{N} \frac{1}{ND(i,x)} \frac{l_1(\hat{P}_i(u^*, v^*))}{\hat{P}_i(u^*, v^*)} \hat{P}_i(u^*, v^*) \right).$$

Likewise, in step S7, the second look-up table $l_2$ is applied to the filtered projection $\hat{P}_I$ at in-plane coordinates $(u^*,v^*)$. This is done for every projection $\hat{P}_I$ labeled by projection index i and for every volume position x determining the respective in-plane coordinates $(u^*,v^*)$. The in-plane coordinates $(u^*,v^*)$ are determined as herein described before with respect to step S2.

Applying the second look-up table $l_2$ to the filtered projection $\hat{P}_I$ at in-plane coordinates $(u^*,v^*)$ and weighting the result with the back-projection weight D and N yields modified weights of the form $$\frac{1}{ND(i,x)} \frac{l_2(\hat{P}_i(u^*, v^*))}{\hat{P}_i(u^*, v^*)}.$$

These modified weights weight the filtered projection $\hat{P}_I$ as second modified weighted contributions of the form $$\sum_{i=1}^{N} \frac{1}{ND(i,x)} \frac{l_2(\hat{P}_i(u^*, v^*))}{\hat{P}_i(u^*, v^*)} \hat{P}_i(u^*, v^*).$$

In step S7, these second modified weighted contributions are accumulated by carrying out the sum over the projection index i.

In a step S8, the inverse second look-up table $\hat{l}_2$ is applied to this result to yield the second modified filtered back-projection density distributions $f_{c2}$ as $$f_{C2}(x) = \hat{l}_2 \left( \sum_{i=1}^{N} \frac{1}{ND(i,x)} \frac{l_2(\hat{P}_i(u^*, v^*))}{\hat{P}_i(u^*, v^*)} \hat{P}_i(u^*, v^*) \right).$$

In step S9, the revised filtered back-projection density distribution $f_{impr}$ that is calculated a weighted linear combination of filtered back-projection density distribution f and the first and second modified filtered back-projection density distributions $f_{c1}$ and $f_{c2}$.

The invention was illustrated and described herein before in detail with reference to example embodiments. It is understood that in particular the description with reference to the figures is for illustrative purposes only and shall not be interpreted in a limiting sense. Variations and combinations may be derived from the information disclosed herein before by the skilled person without departing form the scope or core ideas of present the invention, which are in particular reflected in the appended claims.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method of deriving 3D image data of a reconstruction volume from a plurality of 2D projections by way of filtered back-projection, comprising:
   receiving a plurality of 2D projections of an imaged object, each respective 2D projection, of the plurality of 2D projections, corresponding to a respective projection plane;
   applying a filter to each of the respective 2D projections to yield filtered 2D projections;
   calculating a filtered back-projection density distribution from the filtered 2D projections by way of filtered back-projection;
   calculating, by way of filtered back-projection, at least one modified filtered back-projection density distribution, indicative of outlier values included in the filtered 2D projections; and
   calculating a revised filtered back-projection density distribution as a weighted linear combination of the filtered back-projection density distribution calculated and the at least one modified filtered back-projection density distribution calculated,
   wherein the revised filtered back-projection density distribution is calculated as a weighted linear combination of the filtered back-projection density distribution and at least two modified filtered back-projection density distributions, wherein at least one of the modified filtered back-projection density distributions is indicative of high outlier values included in the respective filtered 2D projections and at least another one of the modified filtered back-projection density distributions is indicative of low outlier values included in the respective filtered 2D projections.

2. The computer-implemented method of claim 1, wherein the calculating, by way of filtered back-projection, of the at least one modified filtered back-projection density distribution, indicative of outlier values included in the filtered 2D projections, comprises:

defining at least one look-up table overweighing outlier values in at least a relevant domain;

defining an inverted look-up table, inverse to the look-up table;

determining, for each respective volume position in the reconstruction volume and for each respective 2D projection, respective two-dimensional in-plane coordinates by projecting the respective volume positions onto the projection plane defined by the respective 2D projections;

determining, for each respective volume position in the reconstruction volume and for each respective 2D projection, a respective modified weighted contribution of each of the respective filtered 2D projections, wherein determining the modified weighted contributions includes evaluating the respective filtered 2D projections at the in-plane coordinates corresponding to the respective volume position and applying the look-up table to the respective filtered 2D projections evaluated at the in-plane coordinates; and accumulating, for each respective volume position in the reconstruction volume, the modified weighted contributions of the 2D projections corresponding to different projection planes and applying the inverted look-up table to a result to yield the modified filtered back-projection density distribution.

3. The computer-implemented method of claim 2, wherein the at least one look-up table is at least in parts determined by the characteristics of a function.

4. The computer-implemented method of claim 3, wherein the characteristics of the function determining the at least one look-up table at least in parts is at least one of a slope of the function, a curvature of the function and a zero of the function.

5. The computer-implemented method of claim 4, wherein the function determining the at least one look-up table is at least in parts a polynomial function, a monomial function or a power function.

6. The computer-implemented method of claim 3, wherein the function determining the at least one look-up table is at least in parts a polynomial function, a monomial function or a power function.

7. The computer-implemented method of claim 2, wherein the at least one look-up table is globally defined or depends on the 2D projection or on a sub-region within the 2D projection.

8. The computer-implemented method of claim 2, wherein the calculating of the at least one modified filtered back-projection density distribution indicative of low outlier values included in the filtered 2D projections comprises defining at least one second look-up table overweighing high outlier values in at least a relevant domain;

defining an inverted second look-up table, inverse to the at least one second look-up table;

determining, for each respective volume position in the reconstruction volume and for each respective 2D projection, respective two-dimensional in-plane coordinates by projecting the respective volume positions onto the projection plane defined by the respective 2D projections; and determining, for each respective volume position in the reconstruction volume and for each respective 2D projection, a respective second modified weighted contribution of each of the respective filtered 2D projections, wherein the determining of the second modified weighted contributions includes evaluating the filtered 2D projections at the in-plane coordinates corresponding to the respective volume position and applying the at least one second look-up table to the respective filtered 2D projections evaluated at the in-plane coordinates; and accumulating, for each respective volume position in the reconstruction volume, the second modified weighted contributions of the 2D projections corresponding to different projection planes and applying the inverted second look-up table to a result to yield the second modified filtered back-projection density distribution.

9. The computer-implemented method of claim 2, wherein the at least one look-up table is at least in parts determined by the characteristics of a function.

10. The computer-implemented method of claim 9, wherein the characteristics of the function determining the at least one look-up table at least in parts is at least one of a slope of the function, a curvature of the function and a zero of the function.

11. The computer-implemented method of claim 2, wherein the calculating of the revised filtered back-projection density distribution as the weighted linear combination of the filtered back-projection density distribution and the at least one modified filtered back-projection density distribution includes determining at least one weight for the at least one modified filtered back-projection density distribution, and wherein the at least one weight is globally defined or depends on a sub-region of the reconstruction volume.

12. The computer-implemented method of claim 1, wherein the calculating of the at least one modified filtered back-projection density distribution indicative of high outlier values included in the respective filtered 2D projections comprises:

defining at least one first look-up table overweighing high outlier values in at least a relevant domain;

defining an inverted first look-up table, inverse to the first look-up table; determining, for each respective volume position in the reconstruction volume and for each respective 2D projection, respective two-dimensional in-plane coordinates by projecting the respective volume positions onto the projection plane defined by the respective 2D projections;

determining, for each respective volume position in the reconstruction volume and for each respective 2D projection, a respective first modified weighted contribution of each of the respective filtered 2D projections, wherein the determining of the first modified weighted contributions includes evaluating the respective filtered 2D projections at the in-plane coordinates corresponding to the respective volume position and applying the first look-up table to the respective filtered 2D projections evaluated at the in-plane coordinates; and accumulating, for each respective volume position in the reconstruction volume, the first modified weighted contributions of the respective 2D projections corresponding to different projection planes and applying the inverted first look-up table to a result to yield the first modified filtered back-projection density distribution.

13. The computer-implemented method of claim 12, wherein the calculating of the at least one modified filtered back-projection density distribution indicative of low outlier values included in the filtered 2D projections comprises defining at least one second look-up table overweighing high outlier values in at least a relevant domain;

defining an inverted second look-up table, inverse to the at least one second look-up table;
    determining, for each respective volume position in the reconstruction volume and for each respective 2D projection, respective two-dimensional in-plane coordinates by projecting the respective volume positions onto the projection plane defined by the respective 2D projections;
    determining, for each respective volume position in the reconstruction volume and for each respective 2D projection, a respective second modified weighted contribution of each of the respective filtered 2D projections, wherein the determining of the second modified weighted contributions includes evaluating the filtered 2D projections at the in-plane coordinates corresponding to the respective volume position and applying the at least one second look-up table to the respective filtered 2D projections evaluated at the in-plane coordinates; and
    accumulating, for each respective volume position in the reconstruction volume, the second modified weighted contributions of the 2D projections corresponding to different projection planes and applying the inverted second look-up table to a result to yield the second modified filtered back-projection density distribution.

14. The computer-implemented method of claim 1, wherein the 3D image data is a tomography or tomosynthesis reconstruction from the plurality of 2D projections.

15. The computer-implemented method of claim 1, wherein the plurality of 2D projections is a tomography or tomosynthesis image data set.

16. The computer-implemented method of claim 15, wherein the plurality of 2D projections is an image data set obtained via medical or non-medical imaging.

17. The computer-implemented method of claim 16, wherein the plurality of 2D projections is an image data set including at least one of a mammography, a computed tomography, a positron emission tomography or a single-photon emission computed tomography, an industrial computed tomography, a non-destructive testing of a fabricated or manufactured good and a homeland security application.

18. The computer-implemented method of claim 1, wherein the calculating of the filtered back-projection density distribution from the filtered 2D projections by way of filtered back-projection, comprises,
    determining, for each respective volume position in the reconstruction volume and for each respective 2D projection, respective two-dimensional in-plane coordinates by projecting the volume positions onto the projection plane defined by each of the respective 2D projections;
    determining, for each respective volume position in the reconstruction volume and for each respective 2D projection, a weighted contribution of each of the respective filtered 2D projections, wherein the determining of the weighted contributions includes evaluating the respective filtered 2D projections at the in-plane coordinates corresponding to the respective volume position; and
    calculating the filtered back-projection density distribution from the respective filtered 2D projections by accumulating the weighted contributions of the respective 2D projections corresponding to different projection planes.

19. The computer-implemented method of claim 1, wherein the calculating of the revised filtered back-projection density distribution as the weighted linear combination of the filtered back-projection density distribution and the at least one modified filtered back-projection density distribution includes determining at least one weight for the at least one modified filtered back-projection density distribution, and wherein the at least one weight is globally defined or depends on a sub-region of the reconstruction volume.

20. The computer-implemented method of claim 19, wherein the at least one weight is determined by way of a volume-domain cost function.

21. A non-transitory computer readable medium storing instructions, when executed on a processor, cause the processor to carry out the computer-implemented method of claim 1.

* * * * *